(12) United States Patent
Zakelj et al.

(10) Patent No.: US 10,675,157 B2
(45) Date of Patent: Jun. 9, 2020

(54) LUMBAR STAND-ALONE SPINE IMPLANT

(71) Applicant: Life Spine, Inc., Huntley, IL (US)

(72) Inventors: Paul C. Zakelj, Chicago, IL (US);
Adam Goon, Denver, CO (US);
Gregory Palagi, Geneva, IL (US)

(73) Assignee: Life Spine, Inc., Huntley, IL (US)

( * ) Notice: Subject to any disclaimer, the term of this patent is extended or adjusted under 35 U.S.C. 154(b) by 260 days.

(21) Appl. No.: 15/936,398

(22) Filed: Mar. 26, 2018

(65) Prior Publication Data
US 2018/0289497 A1  Oct. 11, 2018

Related U.S. Application Data

(60) Provisional application No. 62/482,141, filed on Apr. 5, 2017, provisional application No. 62/528,623, filed on Jul. 5, 2017.

(51) Int. Cl.
*A61F 2/44* (2006.01)
*A61B 17/86* (2006.01)
*A61F 2/46* (2006.01)
*A61F 2/30* (2006.01)

(52) U.S. Cl.
CPC .......... *A61F 2/4455* (2013.01); *A61F 2/442* (2013.01); *A61F 2/447* (2013.01); *A61F 2/4611* (2013.01); *A61B 17/86* (2013.01); *A61B 2017/8655* (2013.01); *A61F 2002/30062* (2013.01); *A61F 2002/30593* (2013.01); *A61F 2002/30787* (2013.01); *A61F 2002/30904* (2013.01); *A61F 2220/0041* (2013.01)

(58) Field of Classification Search
CPC ...... A61F 2/442; A61F 2/4455; A61F 2/4611; A61F 2/447
See application file for complete search history.

(56) References Cited

U.S. PATENT DOCUMENTS

| | | | | |
|---|---|---|---|---|
| 2005/0216081 A1* | 9/2005 | Taylor | .................. | A61F 2/4425 623/17.11 |
| 2008/0312742 A1* | 12/2008 | Abernathie | ............. | A61F 2/447 623/17.16 |
| 2010/0268339 A1* | 10/2010 | Malinin | .................. | A61F 2/447 623/17.11 |
| 2012/0330419 A1* | 12/2012 | Moskowitz | ............. | A61F 2/447 623/17.16 |
| 2014/0046447 A1* | 2/2014 | Dunworth | .......... | A61B 17/7059 623/17.16 |
| 2015/0032220 A1* | 1/2015 | Tyber | .................... | A61F 2/4465 623/23.5 |

* cited by examiner

*Primary Examiner* — Christian A Sevilla
(74) *Attorney, Agent, or Firm* — Foley & Lardner LLP

(57) ABSTRACT

A lumbar spine implant has a body with bone screw bores that angle from a metal faceplate situated at an end of the body, the bone screw bores sized such that the bone screw bores become threaded during introduction of a bone screw thereby providing a locking mechanism to prevent the bone screw from backing out. The faceplate also provides a pocket for each bone screw that prevents the bone screw head from advancing through the implant body. The lumbar spine implant has four bone screw bores, two of which extend from the faceplate to the upper side of the body, and two of which extend from the faceplate to the lower side of the body. More or less bone screw bores may be provided. Preferably, but not necessarily, the direction of the bone screw bores are staggered from one lateral side to another lateral side of the body.

18 Claims, 2 Drawing Sheets

LUMBAR STAND-ALONE SPINE IMPLANT

CROSS-REFERENCE TO RELATED APPLICATIONS

This U.S. non-provisional patent application claims the benefit of and/or priority under 35 U.S.C. § 119(e) to U.S. provisional patent application Ser. No. 62/482,141 filed Apr. 5, 2017 titled "Lumbar Stand-Alone Spine Implant," and U.S. provisional patent application Ser. No. 62/528,623 filed Jul. 5, 2017 titled "Lumbar Stand-Alone Spine Implant," the entire contents of both of which are specifically incorporated herein by reference.

FIELD OF THE INVENTION

The present invention relates to devices for orthopedic surgery of the spine and, particularly, to lumbar spine implants.

BACKGROUND OF THE INVENTION

Many people contend with spine issues as a result of age, disease, and trauma, as well as congenital and acquired complications and conditions. While some of these issues can be alleviated without surgery, other issues necessitate surgery. Issues with the lumbar region of the spine such as decompression and stabilization can be addressed with lumbar implants. One type of lumbar implant is placed within the interbody or disc space once disc tissue has been removed. The lumbar implant is typically secured to one or both of the upper and lower vertebrae. Bone graft may or may not be used with the lumbar implant for vertebral fusion which stops all movement between vertebrae.

The purpose of a lumber implant is to maintain disc height between vertebrae to help prevent nerve compression, and restore and preserve the natural alignment of the lumbar spine, promote spinal fusion. In some cases the lumbar implant may be a holder or carrier for fusion material. In other cases the lumbar implant may stand alone to provide structural stability.

It is an object of the present invention to provide a stand-alone spine implant. It is further an object of the present invention to provide a stand-alone lumbar spine implant. Other object(s) of the present invention are contemplated.

SUMMARY OF THE INVENTION

A stand-alone spine implant is provided, particularly, but not necessarily, for the lumbar region of the spine, the principles of which may be utilized in stand-alone spine implants for other regions of the spine.

The stand-alone lumbar spine implant is characterized by a body that is preferably, but not necessarily, made of PEEK or a similar bio-compatible material, the body having bone screw bores that angle from a preferably, but not necessarily, metal or hard faceplate situated at an end of the body to an upper side of the body and to a lower side of the body, the bone screw bores sized such that the bone screw bores become threaded during introduction of a bone screw thereby providing a locking mechanism to prevent screw backout, the faceplate providing a pocket for each bone screw that prevents the bone screw head from advancing through the implant body.

The stand-alone lumbar spine implant has four bone screw bores, two of which extend from the faceplate to the upper side of the body, and two of which extend from the faceplate to the lower side of the body. More or less bone screw bores may be provided. Preferably, but not necessarily, the direction of the bone screw bores are staggered from one lateral side to another lateral side of the body.

Preferably, but not necessarily, the upper and lower surfaces of the body include serrations, teeth or the like. The serrations, teeth or the like preferably, but not necessarily, are directional.

Preferably, but not necessarily, the body is wedge shaped with the end supporting the faceplate wider than an opposite end of the body.

The faceplate is preferably, but not necessarily, titanium. Other similar materials may be used.

Further aspects of the present invention will become apparent from consideration of the figures and the following description of the invention. A person skilled in the art will realize that other forms of the invention are possible and that the details of the invention can be modified in a number of respects without departing from the inventive concept. The following figures and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

It should be appreciated that dimensions of the components, structures, and features of the present stand-alone lumbar spine implant can be altered as desired.

DETAILED DESCRIPTION OF THE INVENTION

Figure 1:
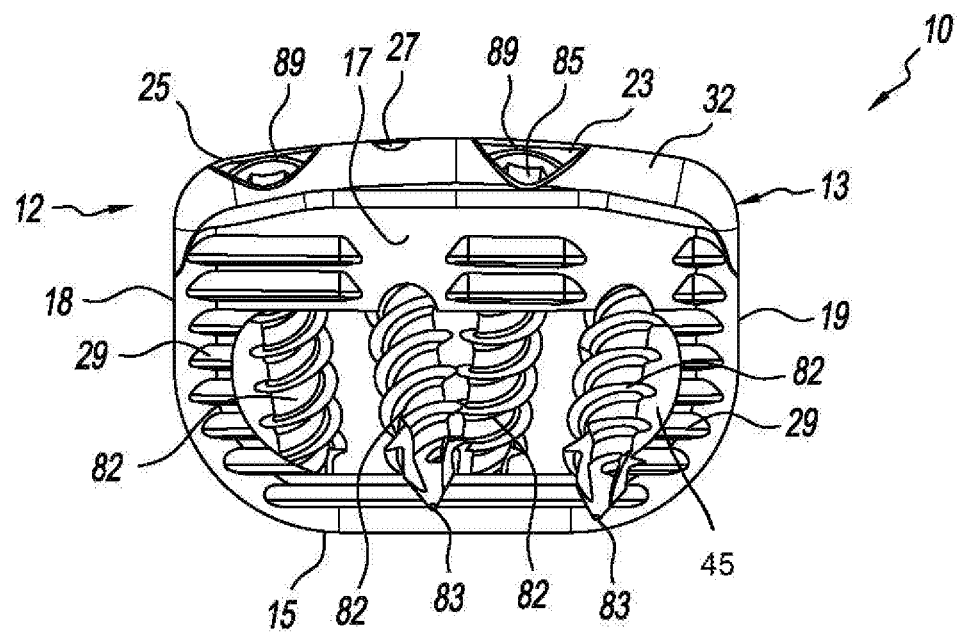
FIG. 1 is an isometric view of a stand-alone lumbar spine implant fashioned in accordance with the present principles with bone screws installed therein.
Figure 2:
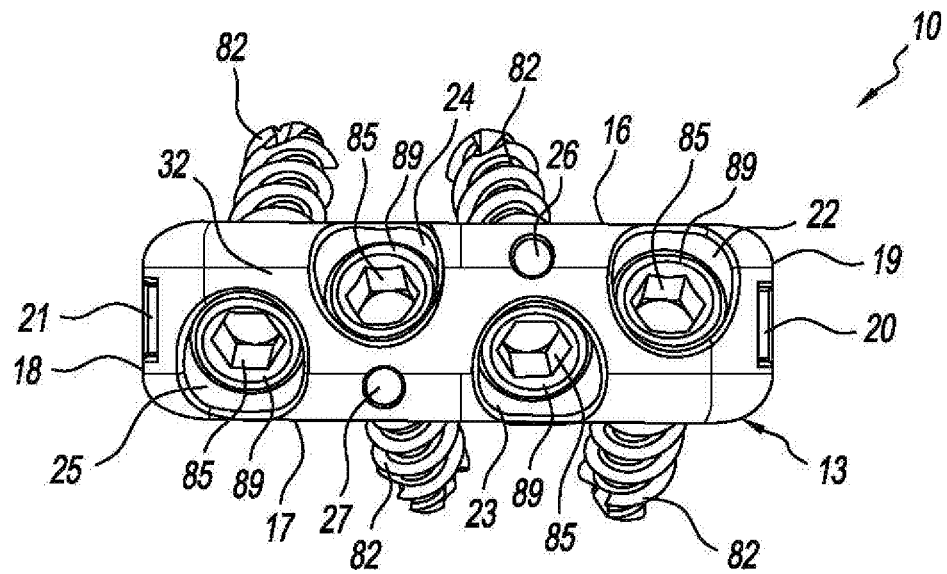
FIG. 2 is a top plan view of the stand-alone lumbar spine implant and bone screws of FIG. 1.
Figure 3:
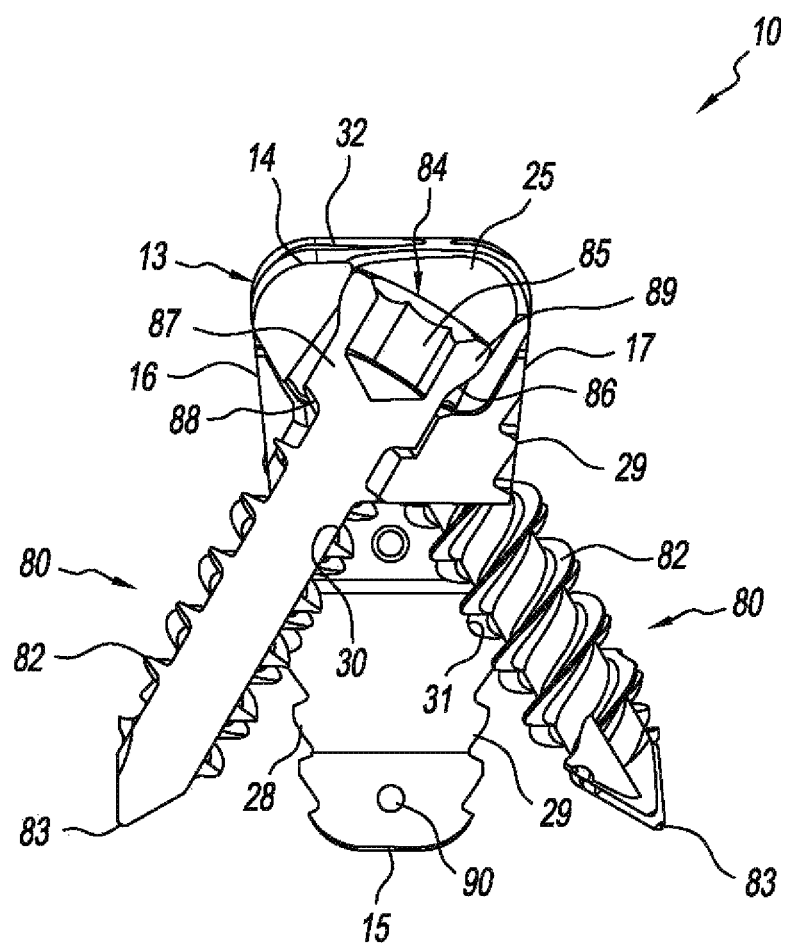
FIG. 3 is a lateral side sectional view of the stand-alone lumbar spine implant and bone screws of FIG. 1.

Referring to FIGS. 1-3, the numeral 10 designates a stand-alone lumbar implant with bone screws. The lumbar spine implant with bone screws (lumbar implant system) 10 is characterized by a lumbar spine (lumbar) implant 12 and a plurality of bone screws 80.

Each bone screw 80 is characterized by an externally threaded shaft 82 with a tip 83 at one end of the shaft 82 and a head 84 at the other end of the shaft 82. The threads of the shaft 82 are configured to engage bone, and particularly vertebral bone. The head 84 is generally cylindrical and has a socket 85 in its upper surface that is configured to receive a like configured installation tool (not shown). The socket 85 may be configured as a hexalobe, hexagon, or other shape. A lip 89 is formed about an upper periphery of the head. Axially below the lip 89 is an inwardly angled portion 86 that tapers to a neck 87. Axially below the neck 87 is a further inwardly angled portion 88 that then tapers to the shaft 82. The bone screw 80 is formed of a suitable bio-compatible material such as, but not limited to, titanium, stainless steel, or an alloy of either. Other configurations of bone screws may be used.

The lumbar spine implant 12 is characterized by a body 13 preferably, but not necessarily, formed of PEEK or another similar bio-compatible material. The body 13 is fashioned generally as a wedge having an upper side 16, a lower side 17 opposite to the upper side 16, a first lateral side 18, a second lateral side 19 that is opposite to the first lateral side 18, a first end 14, and a second end 15 opposite to the first end 14, the nomenclature first, second, upper and lower being arbitrary. Being wedge-shaped, the first end 14 is wider than the second end 15. The body 13 further has an opening 45 that extends from the upper side 16 to the lower side 17. The opening 45 allows the bone screws to project from and angle out of the body 13 for anchoring into vertebral bone or other structure.

The upper side 16 has serrations, teeth, grooves or the like (serrations) 28 extending from the first lateral side 18 to the second lateral side 19 and spaced generally from the second end 15 to the first end 14. The lower side 17 likewise has serrations, teeth, grooves or the like (serrations) 29 extending from the first lateral side 18 to the second lateral side 19 and spaced generally from the second end 15 to the first end 14. The serrations 28, 29 allow the second end 15 and thus the lumbar spine implant 12 to be easily inserted into a spinal cavity but resists extrication of the lumbar spine implant 12 from the spinal cavity.

The second end 14 has a faceplate 32 that is preferably, but not necessarily, formed of metal such as, but not limited to, titanium, stainless steel or the like that provides a hard or relatively hard surface. The faceplate 32 includes a first notch 21 at the first lateral side 18 and a second notch 20 at the second lateral side 19, the notches 19, 20 allowing the reception of an installation tool (not shown). The implant 12 is structured to accept a plurality of the bone screws 80 for attaching to and stabilizing the implant 12 relative to upper and lower vertebrae (not shown). In the embodiment shown, the implant 12 is structured to accept four (4) bone screws 80. The faceplate 32 thus has four (4) angled pockets 22, 23, 24, 25 with open bottoms to accept four (4) bone screws 80. Each angled pocket 22, 23, 24, 25 is sized to allow the threaded shaft 82 of the bone screw 80 to extend through the pocket and out of its open bottom but provide a seat for the head 84 of the bone screw 80 (see, e.g., FIG. 3), and, particularly, to capture the lip 89 of the head 84, to stop the bone screw from advancing through the body 13.

As best seen in FIG. 2, the four (4) pockets are spaced along the faceplate 32 from the first lateral side 18 to the second lateral side 19 in a staggered pattern relative to a centerline of the faceplate 32 as taken from the second lateral side 19 to the first lateral side 18. The first and third pockets 22, 24 are angled such that the received bone screw 80 extends from the lower side 17 of the body 13, while the second and fourth pockets 23, 25 are angled such that the received bone screw 80 extends from the upper side 18 of the body 13. The bone screws 80 extending from the lower side 17 of the body 13 are received in a lower vertebrae (not seen) while the bone screws 80 extending from the upper side 18 of the body 13 are received in an upper vertebrae (not seen). It should be appreciated that the present lumbar implant 12 may utilize more or less bone screws, and in a different staggered pattern for attachment to an upper and lower vertebrae.

The implant body 13 preferably, but not necessarily, includes a bore for receiving each bone screw that is underneath the opening of a pocket (22, 23, 24, 25) of the faceplate 32 and exiting the upper or lower side 18, 17, each bore sized smaller than the threaded bone screw shaft 82 such that the threading of the shaft creates its own threading through the bore (i.e. taps the bore) and thus the implant body 13 during introduction of the bone screw. Internal bore threading 30 for the pocket 25 and internal bore threading 31 for the pocket 24 is shown in FIG. 3. In another form, the implant body 13 initially has no bores underneath the open pockets of the implant 13. Introduction of a bone screw 80 into a pocket of the faceplate creates the threaded bore in the implant. In both cases, the creation of threading or tapping within the bone screw bore of the implant body 13 functions as a locking mechanism for the bone screw 80 to prevent bone screw backout.

The implant 12 further includes a first bore 26 in the faceplate 32 and into the body 13, and a second bore 27 in the faceplate 32 and into the body 13. The first and second bores 26, 27 allow introduction of an installation aiding device, e.g. providing instrument alignment and engagement. As seen in FIG. 3, a hole/bore 90 allows for the introduction and retention of a radiographic marker (not shown).

It should be appreciated that dimensions of the components, structures, and/or features of the present lumbar spine implant may be altered as desired within the scope of the present disclosure.

What is claimed is:

1. A spine implant comprising:
a body made from a bio-compatible plastic and defining a front, a back, a first lateral side, a second lateral side, an upper side, a lower side, an opening extending through the body from the upper side to the lower side, and a plurality of bores extending from and into the front of the body, each bore angled relative to the front of the body so as to project a received bone screw from the opening of the body at the angle of the bore, and sized to cause the received bone screw to self-thread into the front of the body to lock position of the bone screw relative to the body; and
a faceplate made of a biocompatible metal and extending about the front of the body, the faceplate having a plurality of pockets corresponding in number to the plurality of bores of the front of the body, each pocket configured to retain and prevent a head of the received bone screw from advancing through the front of the body.

2. The spine implant of claim 1, wherein the bio-compatible plastic comprises PEEK.

3. The spine implant of claim 1, wherein the bio-compatible metal comprises one of titanium, stainless steel, an alloy of stainless steel, or an alloy of titanium.

4. The spine implant of claim 1, wherein adjacent bores of the front of the body are angled in opposite directions.

5. The spine implant of claim 4, wherein adjacent pockets of the faceplate are angled in opposite directions and the same as the opposite directions of the bores of the front of the body.

6. The spine implant of claim 1, wherein the number of the plurality of bores of the front of the body comprises four.

7. An implant for a lumbar region of a spine, the lumbar implant comprising:
a generally D-shaped body made from a bio-compatible polymer and defining a front, a back, a first lateral side, a second lateral side, an upper side, a lower side, an opening extending through the body from the upper side to the lower side, and a plurality of bores extending from and into the front of the body, each bore angled relative to the front of the body so as to guide a bone screw into projecting a threaded portion thereof from the opening of the body at the same angle as the angle of the bore, and sized to cause the received bone screw to self-thread into the front of the body to lock position of the bone screw relative to the body; and a faceplate made of a biocompatible metal and covering the front of the body, the faceplate having a plurality of pockets corresponding in number to the plurality of bores of the front of the body, each pocket configured to prevent a head of a received bone screw from advancing into the front of the body.

8. The lumbar implant of claim 7, wherein the biocompatible polymer comprises PEEK.

9. The lumbar implant of claim 7, wherein the biocompatible metal comprises one of titanium, stainless steel, an alloy of stainless steel, or an alloy of titanium.

10. The lumbar implant of claim 7, wherein adjacent bores of the front of the body are angled in opposite directions.

11. The lumbar implant of claim 10, wherein adjacent pockets of the faceplate are angled in opposite directions that are the same as the opposite directions of the bores of the front of the body.

12. The lumbar implant of claim 7, wherein the number of the plurality of bores of the front of the body comprises four.

13. An interbody implant for a lumbar region of a spine, the lumbar interbody implant comprising:
a D-shaped body made from a bio-compatible plastic and defining a front, a back, a first lateral side, a second lateral side, an upper side, a lower side, a central opening extending through the body from the upper side to the lower side, and a plurality of bores extending into the front of the body, each bore angled relative to the front of the body so as to guide a bone screw into projecting a threaded portion of the bone screw from the central opening of the body at the same angle as the angle of the bore, and sized to cause the received bone screw to self-thread into the front of the body to lock position of the bone screw relative to the body; and
a faceplate made of a biocompatible metal and covering the front of the body, the faceplate having a plurality of pockets corresponding in number to the plurality of bores of the front of the body, each pocket configured to prevent a head of a received bone screw from advancing into the front of the body.

14. The lumbar interbody implant of claim 13, wherein the bio-compatible plastic comprises PEEK.

15. The lumbar interbody implant of claim 13, wherein the bio-compatible metal comprises one of titanium, stainless steel, an alloy of stainless steel, or an alloy of titanium.

16. The lumbar interbody implant of claim 13, wherein adjacent bores of the front of the body are angled in opposite directions.

17. The lumbar interbody implant of claim 16, wherein adjacent pockets of the faceplate are angled in opposite directions that are the same as the opposite directions of the bores of the front of the body.

18. The lumbar interbody implant of claim 13, wherein the number of the plurality of bores of the front of the body comprises four.

* * * * *